United States Patent [19]
Scheldrup

[11] Patent Number: 6,019,757
[45] Date of Patent: Feb. 1, 2000

[54] ENDOLUMINAL ELECTRO-OCCLUSION DETECTION APPARATUS AND METHOD

[75] Inventor: Ronald W. Scheldrup, Menlo Park, Calif.

[73] Assignee: Target Therapeutics, Inc., Fremont, Calif.

[21] Appl. No.: 08/499,525

[22] Filed: Jul. 7, 1995

[51] Int. Cl.[7] .................................................. A61B 17/36
[52] U.S. Cl. .............................. 606/49; 606/32; 606/40; 606/135
[58] Field of Search ............................ 606/32–34, 37–42, 606/45–50, 135; 607/154, 156, 98, 101

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,675,655 | 7/1972 | Sittner . |
| 3,753,700 | 8/1973 | Harrison et al. . |
| 3,868,956 | 3/1975 | Alfidi et al. . |
| 4,057,063 | 11/1977 | Gieles et al. . |
| 4,416,276 | 11/1983 | Newton et al. . |
| 4,494,539 | 1/1985 | Zentani et al. . |
| 4,565,200 | 1/1986 | Cosman . |
| 4,582,057 | 4/1986 | Auth et al. . |
| 4,700,701 | 10/1987 | Montaldi . |
| 4,709,701 | 12/1987 | Weber ........................................ 607/98 |
| 4,739,768 | 4/1988 | Engelson . |
| 4,884,575 | 12/1989 | Sanders . |
| 4,907,589 | 3/1990 | Cosman . |
| 4,974,595 | 12/1990 | Nordenström . |
| 4,994,069 | 2/1991 | Ritchart et al. . |
| 5,057,105 | 10/1991 | Malone et al. . |
| 5,067,491 | 11/1991 | Taylor, II et al. . |
| 5,078,736 | 1/1992 | Behl . |
| 5,122,136 | 6/1992 | Guglielmi et al. ........................ 606/32 |
| 5,167,658 | 12/1992 | Ensslin . |
| 5,170,802 | 12/1992 | Mehra . |
| 5,174,295 | 12/1992 | Christian et al. . |

(List continued on next page.)

FOREIGN PATENT DOCUMENTS 0407057  1/1991  European Pat. Off. .
WO 97/30642  8/1997  WIPO .

OTHER PUBLICATIONS

Becker et al. "Long–Term Occlusion of the Porcine Cystic Duct by Means of Endoluminal Radio–Frequency Electrocoagulation" *Radiology* (1988) 167:63–68.

Bubien et al., "What you Need to Know About Radiofrequency Ablation" *AJN* (Jul. 1993) pp. 30–36.

El–Sabban et al., "Stability of Thrombosis Induced by Electrocoagulation of Rat Middle Cerebral Artery" *Stroke* (1994) 25:2241–2245.

Gold et al., "Transarterial Electrocoagulation Therapy of a Pseudoaneurysm in the Head of the Pancreas" *American Journal of Roentgenology* (1975) 125:422–426.

(List continued on next page.)

*Primary Examiner*—Lee Cohen
*Assistant Examiner*—Bryan K. Yarnell
*Attorney, Agent, or Firm*—Morrison & Foerster LLP

[57] ABSTRACT

An apparatus and method for occluding a lumen, such as a vessel, in a mammal using alternating current and monitoring reflected power from the occlusion site to determine vessel constriction and/or electrocoagulation. The apparatus is provided with an alternating current (AC) power generator, a first electrode electrically coupled to the generator, a dispersive electrode electrically coupled to the generator and forming in-part with the generator and the first electrode a drive circuit and a reflected power monitoring circuit coupled to the drive circuit for monitoring power reflected back toward the generator from the first electrode. With this construction, occlusion and/or thermocoagulation can be accurately detected so that the power delivered to the first electrode when positioned in the mammal can be terminated. In this manner, the risk of overheating tissue in the vicinity of the constricted vessel is minimized or eliminated.

15 Claims, 8 Drawing Sheets

U.S. PATENT DOCUMENTS

| | | |
|---|---|---|
| 5,178,618 | 1/1993 | Kandarpa . |
| 5,188,122 | 2/1993 | Phipps et al. .............................. 606/33 |
| 5,190,517 | 3/1993 | Zieve et al. . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson ................................. 606/108 |
| 5,300,068 | 4/1994 | Rosar et al. .............................. 606/32 |
| 5,304,194 | 4/1994 | Chee et al. . |
| 5,304,195 | 4/1994 | Twyford, Jr. et al. . |
| 5,312,415 | 5/1994 | Palermo . |
| 5,341,807 | 8/1994 | Nardella . |
| 5,350,397 | 9/1994 | Palermo et al. . |
| 5,354,295 | 10/1994 | Guglielmi et al. . |
| 5,364,392 | 11/1994 | Warner et al. ............................ 606/34 |
| 5,372,596 | 12/1994 | Klicek et al. ............................. 606/34 |
| 5,380,320 | 1/1995 | Morris . |
| 5,382,259 | 1/1995 | Phelps et al. . |
| 5,405,322 | 4/1995 | Lennox et al. . |
| 5,411,546 | 5/1995 | Bowald et al. . |
| 5,415,657 | 5/1995 | Taymor-Luria . |
| 5,423,810 | 6/1995 | Goble et al. . |
| 5,423,829 | 6/1995 | Pham et al. . |
| 5,437,664 | 8/1995 | Cohen et al. . |
| 5,496,312 | 3/1996 | Klicek ....................................... 606/34 |
| 5,556,396 | 9/1996 | Cohen et al. ............................. 606/42 |
| 5,558,671 | 9/1996 | Yates . |
| 5,562,703 | 10/1996 | Desai . |
| 5,569,241 | 10/1996 | Edwards . |
| 5,569,242 | 10/1996 | Lax et al. . |
| 5,569,245 | 10/1996 | Guglielmi et al. . |
| 5,582,609 | 12/1996 | Swanson et al. . |
| 5,693,082 | 12/1997 | Warner et al. .......................... 607/101 |

OTHER PUBLICATIONS

Kopecky et al., "Percutaneous Transrenal Endoureteral Radio–frequency Electrocautery for Occlusion: Case Report" *Radiology* (1989) 170:1047–1048.

Nath et al., "Basic Aspects of Radiofrequency Catheter Ablation" *J. Cardiovascular Electrophysiol.* (1994) 5:863–876.

Phillips, "Transcatheter Electrocoagulation of Blood Vessels" *Investigative Radiology* (1973) 8:295–304.

Phillips et al., "Experimental Closure of Arteriovenous Fistula by Transcatheter Electrocoagulation" *Diagnostic Radiology* (1975) 115:319–321.

Rish, "Cerebrovascular Accident after Percutaneous rf Thermocoagulation of the Trigeminal Ganglion" *J. Neurosurg.* (1976) 44:376–377.

Tanigawa et al., "Intraarterial Occlusion by Radiofrequency" *Acta Radiologica* (1994) 35:626–628.

Thompson et al., "Transcatheter Electrocoagulation: A Therapeutic Angiographic Technique for Vessel Occlusion," *Investigative Radiology* (1977) 12:146–153.

Thompson et al., "Vessel Occlusion with Transcatheter Electrocoagulation: Initial Clinical Experience" *Diagnostic Radiology* (1979) 133:335–340.

Bowick, "Impedance Matching" *RF Circuit Design* Howard W. Sams & Co., ISBN 0–672–21868 (1993) pp. 66–67, 104–105, 160–161.

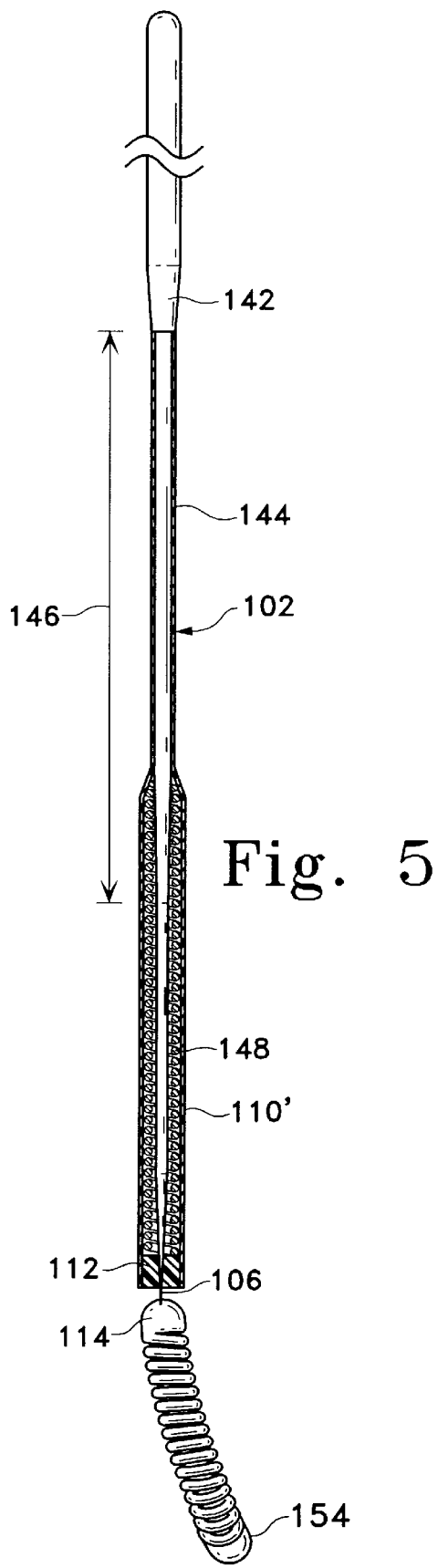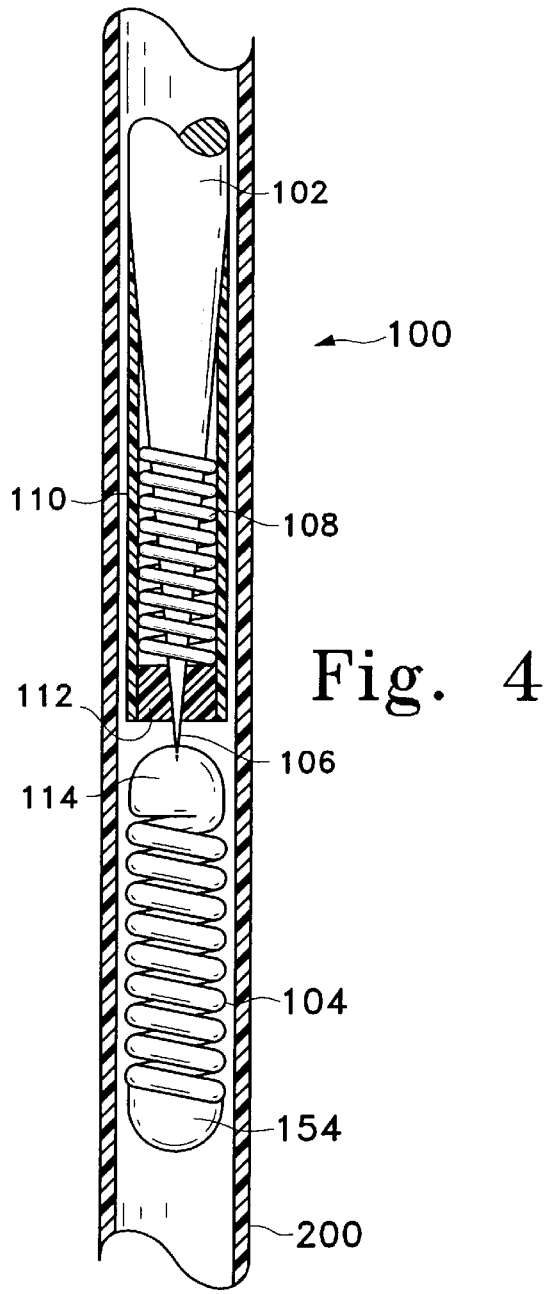

ENDOLUMINAL ELECTRO-OCCLUSION DETECTION APPARATUS AND METHOD

FIELD OF THE INVENTION

The invention relates to the field of endoluminal electro-occlusion. More specifically, the invention involves detecting alternating current induced endoluminal electro-occlusion.

BACKGROUND OF THE INVENTION

A wide variety of medical treatments can be facilitated by occluding body lumens or cavities such as arteries, veins, aneurysms, vascular malformations, arteriovenous fistulas, fallopian tubes, ureters, cystic ducts, or vas deferens. Endovascular occlusion approaches typically involve placing surgical implements or implants within the vasculature of the human body, for example, typically via a catheter (see e.g., U.S. Pat. Nos. 4,884,575 and 4,739,768, both to Engelson), either to block the flow of blood through a vessel making up that portion of the vasculature through the formation of an embolus or to form such an embolus within an aneurysm stemming from the vessel.

Occlusion of vascular structures by endovascular catheters has been realized through the use of detachable balloons, injectable glue, embolic coils, and injectable particles. Detachable balloons are of such a nature that they can only be practically used in large vessels. The use of injectable glue is limited by the difficulty of controllable delivery to the desired occlusion site. The use of injectable particles suffers from their relative invisibility in fluoroscopy and the difficulty in controlling their ultimate disposition at the desired occlusion site.

A highly desirable embolism-forming device that may be introduced into an aneurysm using endovascular placement procedures, is found in U.S. Pat. No. 4,994,069, to Ritchart et al. The device, typically a platinum/tungsten alloy coil having a very small diameter, may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136), discussed below.

U.S. Pat. No. 5,250,071 to Palermo discloses a coil having interlocking clasps with a delivery device, the clasps being secured together by a control wire and released upon withdrawal of the control wire. Another mechanically detachable coil is described in U.S. Pat. No. 5,261,916 to Engelson which discloses a pusher-vasoocclusive coil assembly having a ball on the proximal end of the coil interlockingly engaged with a keyway at the distal end of the pusher. The ball is biased on the coil to be disengaged with the keyway, and is coupled with the keyway by radially enclosing the assembly within a microcatheter. Withdrawal of the microcatheter allows the bias of the ball to disengage the coupling.

U.S. Pat. No. 5,122,136 to Guglielmi et al. discloses an electrolytically detachable coil. The coil is attached to the distal end of an insertion device by a sacrificial joint or link that is electrolytically dissolvable upon application of a small DC current. The return electrode is typically placed on the patient's skin.

U.S. Pat. No. 5,423,829 describes a variation of the Guglielmi detachable coil using an improved sacrificial link between the guidewire and the coil. The size of the sacrificial link is limited to allow more precise placement of the embolic device and facilitate quick detachment. The focussed electrolysis found at the sacrificial site reduces the overall possibility of occurrence of multiple electrolysis sites and liberation of large particles from those sites.

The circuit involved in the electrolytic coil detachment arrangements discussed above generally includes a power source having its positive terminal coupled to the sacrificial link via a guidewire, for example. More specifically, a positive electric current of approximately 0.01 to 2 milliamps is applied to the guidewire which is coupled to the sacrificial link that is intended to undergo electrolytic disintegration and which initially couples the implant (e.g., the vasoocclusion device) to the guidewire. The negative terminal of the power source is typically coupled to an electrode that is placed over and in contact with the patient's skin.

Another return electrode or cathode arrangement is disclosed in U.S. Pat. No. 5,364,295 to Guglielmi et al. In that arrangement, the microcatheter is supplied with an end electrode. More specifically, the electrode extends distally from the microcatheter and is coupled to an electrical conductor or wire disposed along the length of the microcatheter. The wire is ultimately led back to the negative terminal of the power source so that the electrode (ring electrode) is used as the cathode during electrothrombosis instead of an exterior skin electrode.

According to the '295 patent, the electrical currents and electrical current paths which are set up during electrothrombosis formation using the above-described catheter-electrode arrangement are local to the site of application, which allows even smaller currents and voltages to be used to initiate electrothrombosis.

Another embolic device is the liquid coil, which has little or no inherent secondary shape. U.S. Pat. No. 5,690,666 discloses a coil having little or no shape after introduction into the vascular space.

In addition to delivering embolic coils, other well known endoluminal occlusion techniques have involved passing direct current (DC) or alternating current (AC) through tissue to create an occlusive tissue response. Such techniques generally require an occlusion electrode, usually disposed on an endoluminal device within the target lumen or cavity, and a reference electrode, usually comprising a patch on the skin. A DC or AC power source coupled to the electrodes applies direct or oscillating current, respectively, between the two electrodes and through the tissue.

Publications describing the use of DC electrocoagulation for occlusion include: Thompson et al., "Vessel Occlusion with Transcatheter Electrocoagulation: Initial Clinical Experience," *Diagnostic Radiology* at 335 (November 1979); Thompson et al., in "Transcatheter Electrocoagulation: A Therapeutic Angiographic Technique for Vessel Occlusion," *Investigative Radiology* at 146 (March–April 1977); Phillips, "Transcatheter Electrocoagulation of Blood Vessels," *Investigative Radiology* at 295 (September–October 1973); and Phillips et al., "Experimental Closure of Arteriovenous Fistula by Transcatheter Electrocoagulation," *Diagnostic Radiology* 115:319.

As described in the above publications, the occlusion electrode is generally used as the anode and a constant current supply is usually used. The DC current is generally delivered over extended periods of time to achieve coagulation which occludes a lumen. Delivery of 10–15 mA of direct current for a time period ranging from 6–80 minutes has generally been required for DC electrocoagulation. Observed negative implications of this level of direct current over the time required for occlusion have included burns at the electrode sites, electrode fragmentation into patient tissues, and pain requiring administration of Morphine, Demorol, or other pain killers. It is believed that electrothrombosis from DC currents is in part due to attraction of negatively charged platelets to the positively charged occlusion electrode (anode), and in part to a like attraction of platelets to thermally injured and positively charged wall components.

In the case of AC currents used for occlusion, much higher peak currents than those disclosed in DC uses have been safely used to create occlusions. For example, Gold et al., in "Transarterial Electro-coagulation Therapy of a Pseudoaneurysm in the Head of the Pancreas," *American Journal of Roentgenology* (1975) 125(2) :422 disclosed that 500 mA of current in an AC electrocoagulation device was delivered safely in preliminary studies. Nevertheless, radio-frequencies (RF) are generally used for AC occlusion, as lower frequencies have been observed to cause fibrillation.

An example of the tissue response to RF oscillating currents is described by Becker et al. in "Long-Term Occlusion of the Porcine Cystic Duct by Means of Endoluminal Radio-Frequency Electrocoagulation," *Radiology* (1988) 167:63–68. Becker et al. disclose using RF power with bipolar occlusion electrodes to occlude the cystic ducts in pigs. Maximum duration to achieve occlusion was 24 seconds, peak current flow levels ranged from 100 to 425 mA, and all test ducts were occluded with an acute narrowing of the ducts observed. Becker et al. also observed an inherent limitation to their RF technique: adherence of the occlusion electrodes to the tissue at the occlusion site and damage upon subsequent withdrawal of the device from the occlusion.

Another example of the tissue response to "high frequency" electro-occlusion is disclosed in U.S. Pat. No. 4,057,063 to Gieles et al. Gieles et al. disclose coagulating and desiccating the fallopian tubes for sterilization of human females using a "high frequency" generator that is coupled to an electrode fixed to the end of a catheter. Gieles discloses that a series of high frequency pulses causes coagulation, desiccation, and ultimately carbonization of the patient tissue in the fallopian tube.

One mechanism for monitoring the progression of occlusion, disclosed by Gieles et al. (supra), signals a user of an RF occlusion device when the procedure is complete. Upon applying high frequency energy to the target fallopian tube tissue, lamps are energized and extinguished to signal completion of occlusion based upon monitored changes in the rms values of current and voltage delivered by the generator. The RF power generator is then shut down manually by the user when sign al led to do so by the lamps.

U.S. Pat. No. 4,907,589 to Cosman discloses an over-temperature control apparatus for an RF therapeutic heating device. The apparatus provides a combined manual and automatic temperature control of heating of biological tissue by an electrode.

There is a need to provide apparatus for accurately detecting electro-occlusion and an apparatus for automatically terminating the power output in an electro-occlusion device in response to detecting occlusion.

SUMMARY OF THE INVENTION

The present invention involves an apparatus for occluding a lumen, such as a vessel, in a mammal using alternating current AC and monitoring reflected power from the occlusion site to determine vessel constriction and/or electrocoagulation. According to the present invention an apparatus is provided comprising an AC power generator, a first electrode (which preferably is an occlusive implant) electrically coupled to the generator, a dispersive electrode electrically coupled to the generator and forming in-part with said generator and the first electrode a drive circuit and a reflected power monitoring circuit coupled to the drive circuit for monitoring power reflected back toward the generator from the first electrode. With this construction, occlusion and/or thermocoagulation can be accurately detected so that the power delivered to the first electrode when positioned in the mammal can be terminated. In this manner, he risk of overheating tissue adjacent to the constricted vessel is minimized or eliminated.

According to another aspect of the invention, the AC generator is a radio-frequency (RF) generator. RF power advantageously enhances the dielectric heating efficiency of the occlusion device to reduce the requisite power input, while effecting occlusion in a relatively short period of time. Reducing power input minimizes or avoids the risk of thermally damaging tissue in the surrounding environment. It also has been found that RF power facilitates monitoring reflected power.

The method for detecting occlusion of a lumen in a mammal according to the present invention comprises the steps of: (a) delivering a first electrode (which can be any first electrode occlusive implant) to a desired site within the mammal; (b) applying an alternating current to the electrode; and (c) monitoring reflected power from the electrode. The monitored reflected power advantageously indicates when occlusion occurs. According to a particular embodiment of the invention, the method further includes identifying a baseline reflected power signal after step (b) and interrupting the application of alternating current to the first electrode in response to a predetermined change in the monitored reflected power from the baseline signal.

The above is a brief description of some of the features and advantages of the present invention. Other features, advantages and embodiments of the invention will be apparent to those skilled in the art from the following description, accompanying drawings and appended claims.

BRIEF DESCRIPTION OF THE DRAWINGS

FIG. 4 shows an electrolytically detachable occlusion device assembly for use with the apparatus of FIG. 1, illustrating the interconnection between the guidewire, sacrificial link and occlusive device.

FIG. 5 illustrates a further embodiment of the interconnection shown in FIG. 4.

DETAILED DESCRIPTION OF THE PREFERRED EMBODIMENTS

Figure 1:
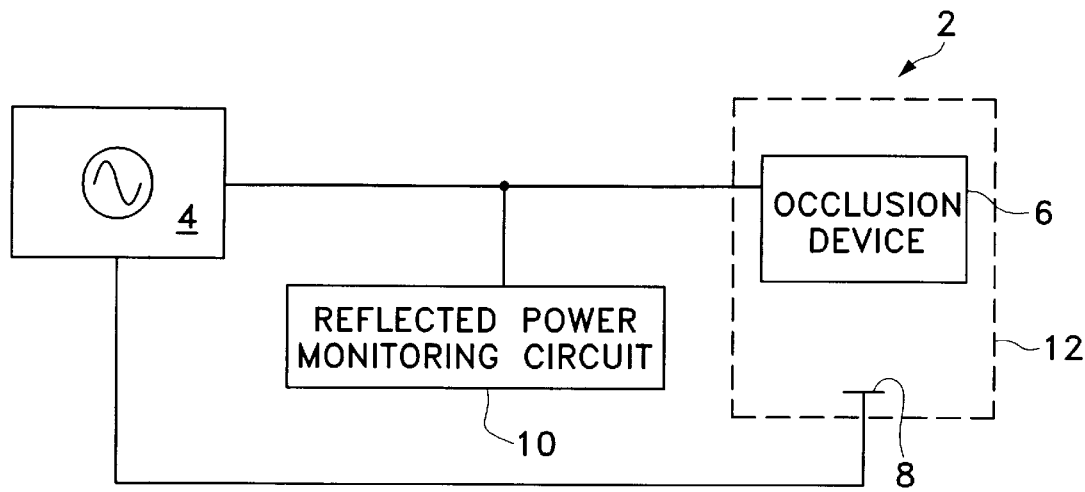
FIG. 1 shows a block diagram of an endoluminal occlusion apparatus constructed according to the principles of the present invention.

Referring to the drawings in detail wherein like numerals indicate like elements, FIG. 1 shows a block diagram of an endoluminal electro-occlusion apparatus 2 constructed according to the principles of the present invention. Electro-occlusion apparatus 2 generally comprises an alternating current (AC) generator 4, an endoluminal occlusion device or implant 6 (which forms an active electrode as will be apparent from the following description), a return or dispersive electrode 8 and a reflected power monitoring circuit (RPM) 10. Although apparatus 2 can be used to occlude various lumens, including fallopian tubes, for example, it will be described in connection with occluding vessels for purposes of simplification.

According to the present invention, endoluminal occlusion device or electrode 6 is conductive and detachably coupled to a conventional conductive delivery wire, core wire or pusher suitable for guiding or delivering the device to or near an endovascular occlusion site in a patient represented in dashed line in FIG. 1 and designated with reference numeral 12. AC generator 4 provides AC current to device 6 via the conductive delivery wire at a power and frequency effective for dielectrically heating the vessel wall around device 6 such that the vessel wall shrinks around the device.

In general, the proteins of the vascular wall are denatured by the heat generated by the power delivered by generator 4 and shrinkage of the vascular wall will occur. For example, it is well known that collagen fibers in the vascular wall are shrinkable at temperatures above 60° C. Carbonization of the blood in the immediate vicinity of the device also can occur at these temperatures.

The power generated by generator 4 is selected to heat the vessel site preferably to a temperature of about 50–120° C. to effect vessel constriction. Preferably the output power of generator 4 is selected to provide a power density of between about 1 W/mm$^2$ to 30 W/mm$^2$ at the interface between occlusion device 6 and the vessel wall at the occlusion site (at voltages from about 2 Vrms–45 Vrms and rms currents of about 0.01 A–0.33 A). It has been found that for a coil-type occlusion device having a length of about 6 mm with a 1 mm long distal insulated tip, a helix diameter of 0.25 mm, and wire size of 0.05 mm, a preferred range of power delivered to the coil is about 0.2 to 5 watts at occlusion device 6. The frequency of the AC generator preferably is in the radio-frequency (RF) range to effect heating at these power ranges, which are preferred to minimize or eliminate risks of fibrillation, for example. The RF power also facilitates monitoring reflected power from the occlusion device to detect, for example, vessel occlusion in accordance with the present invention as described below.

RPM circuit 10 monitors the reflected power from device 6 and preferably includes a processor to automatically turn off or interrupt AC generator 4 when a reflected power value change indicative of vessel constriction is detected. The delivery wire can then be decoupled from device 6 and removed from the patient as will be described in more detail below. As discussed above, the AC generated by generator 4 preferably is in the RF range to facilitate reflected power monitoring. 4 MHz, for example, provides suitable results when using an electrolytically detachable coil dimensioned as noted above. However, other radio frequencies can be used.

The electro-occlusion apparatus of the present invention can be used with various occlusion device assemblies including mechanically detachable coil assemblies, for example, as disclosed in U.S. Pat. Nos. 5,234,437; 5,250,071; and 5,261,916; and electrolytically detachable coils as disclosed, for example, in U.S. Pat. Nos. 5,122,136 and 5,226,911. (The disclosures of these patents are hereby incorporated by reference in their entirety.)

Figure 2:
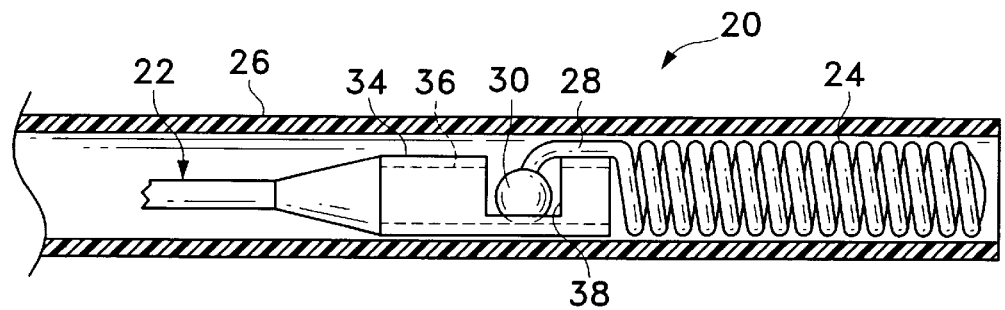
FIGS. 2 and 3 show a mechanically detachable occlusion device assembly for use with the apparatus of FIG. 1, in attached and detached states, respectively.
Figure 3:
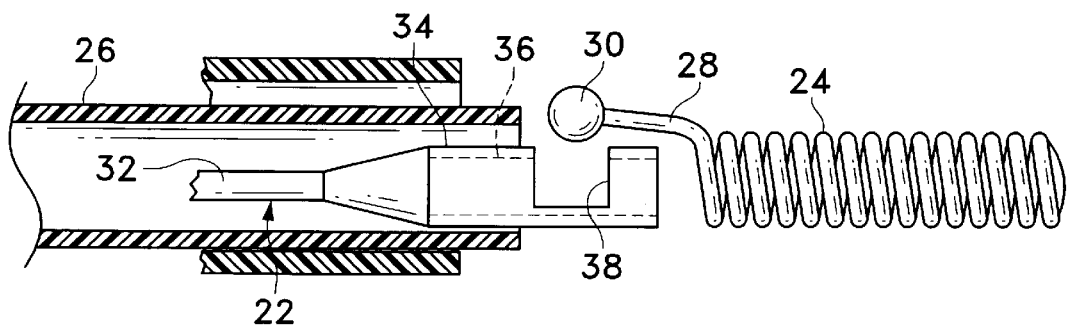

Referring to FIGS. 2 and 3, one suitable mechanically detachable coil assembly 20 is shown for purposes of example. As described in U.S. Pat. No. 5,261,916, assembly 20 generally includes pusher or delivery wire 22, occlusive implant or vasoocclusive coil 24 and catheter or sleeve 26. The end of proximal coil segment 28 carries a sphere or ball 30. Pusher 22 includes a central core 32 and an enlarged cylindrical end 34 having an axial bore 36 and keyway 38 for receiving ball 30. Catheter 26 maintains the ball in the keyway as the pusher and coil are advanced therethrough (FIG. 2).

In operation, AC generator 4 is selectively coupled to conductive occlusive coil 24 via delivery wire 22 so that AC power can be delivered to the coil via enlarged distal end 34 and coil 24. This can be accomplished by clamping a lead from AC generator 4 to the proximal end portion (not shown) of delivery wire 22. Dispersive or return electrode 8, which preferably is a conventional large patch patient electrode, is secured to the patient to form the power return. The coil assembly is advanced so that the keyway and ball are aligned with the distal end of the catheter which has been positioned so that the coil extends from the catheter at the desired site. Once the coil is so positioned, AC generator 4 is activated to effect vessel constriction around the coil. After vessel constriction is detected and the generator output interrupted, as will be discussed in further detail below, the coil can be detached by fixing the delivery wire position and retracting the catheter. When the keyway and ball are free of the catheter, the outward radial bias of segment 28 causes the ball to move out of the keyway, thereby uncoupling the coil from the pusher (FIG. 3). The catheter and delivery wire may then be removed.

The outward radial bias of segment 28 also facilitates forming effective contact between cylindrical end 34 and ball 30 to provide an electrical connection therebetween before the coil is deployed. The elements of coil assembly 24 are selected to provide the requisite conductivity. In addition, the interface between the guidewire and the coil may be further electrically coupled, such as by soldering as would be apparent to one of ordinary skill. However, any such additional connection must be sufficiently weak to allow the biasing force of segment 28 to separate the coil from the pusher for detachment.

Referring to FIGS. 4 and 5, a suitable electrolytically detachable coil assembly 100 showing a preferred coil construction is shown. Assembly 100 generally includes a guidewire (or core or delivery wire) 102, an occlusive implant or occlusion device 104 (e.g., a coil as shown in the drawings) and a sacrificial link 106 that couples the implant to the guidewire, as will be described in more detail below.

Referring to FIG. 4, an enlarged view of a portion of implant assembly 100 is shown illustrating the interconnection between the guidewire, sacrificial link and implant for facilitating electrolytic detachment of the implant from the guidewire. Specifically, guidewire 102 tapers at its distal end to a point which is soldered into the proximal end of implant or coil 104. Coil 104 preferably is radiopaque physiologically compatible material such as platinum, tungsten, gold, iridium or alloys of these materials.

Guidewire 102, which preferably is stainless steel, typically is approximately 10–30 mils in diameter and 50–300 cm in length from the entry site outside the body to sacrificial link 106. As shown in FIG. 4, sacrificial link 106 is the exposed portion of guidewire 102 that extends beyond insulator 112. Link 106 is of a material, such as stainless steel, which is susceptible to electrolytic dissolution in blood.

Guidewire 102 preferably is covered with an insulating material from its proximal end to its distal exposed portion which forms sacrificial link 106. Suitable insulating materials include TEFLON, polyurethane, polyethylene, polypropylene, or other suitable polymeric material.

In a first embodiment, link 106 is not coated with an electrical insulator. In this case, the length of link 106 preferably is approximately equal to its diameter so that the electrolytic surface present after the vasoocclusive device is released is not substantially greater than would be a circle having the diameter of the link (link diameters may range from about 2–4 mils, for example). This configuration reduces the likelihood of multiple etch sites on the link. Alternatively, link 106 can be coated with a polymer, preferably parylene (polyxylylene), and a UV laser (excimer type) used to cut a circumferential groove, having a width of about 1–3 mil in the polymer, to expose only a small ring of the link and localize the disintegration area. Preferably, the groove is immediately adjacent to the interconnection between the link and implant.

Implant delivery assembly 100 also includes insulators 110 and 112 and coil 108, which is coupled at its proximal end to the guidewire by soldering, for example. Coil 108 is designed to provide some column strength to guidewire 102 while not detrimentally affecting the flexibility of the tapered portion of the guidewire. Obviously, in the area where support coil 108 is soldered to guidewire 102, the coating on the guidewire is not present, allowing the solder to adhere to metal surfaces.

Insulators 110 and 112 are provided at the distal end portion of guidewire 102 and serve to further remove stainless steel coil 108 from contact with the blood during electrolysis. In the illustrative embodiment, insulators 110 and 112 comprise a sleeve and plug, respectively. Preferably, end plug 112 and sleeve 110 are adhesively attached to each other to form an electrically insulating or electrolysis-tight housing about coil 108. End plug 112 and sleeve 110 form a generally planar surface which is generally perpendicular to the axis of the guidewire 102 (FIG. 4). The shape of the surface is not critical except to the extent it allows reasonably free access of the blood to sacrificial link 106. Curved, slotted and other variations of the end surface are also contemplated to be used in this invention. As noted above, the distal end of guidewire 102 is inserted into the solder joint 114 forming the proximal end of vasoocclusive device 104.

Referring to FIG. 5, one suitable configuration for guidewire 102 is shown. In this embodiment, guidewire 102 includes tapered or conical section 142, section 144 which extends along a length of the guidewire designated with reference numeral 146 and section 148. Section 144 gradually narrows down to thinner section 148. Guidewire 102 is delivered to the desired site via a catheter 200 (shown in FIG. 4) and is typically 50–200 cm in length down to sacrificial link 106. Catheter 200 and guidewire 102 can be provided with radiopaque markers to provide a guidewire locating mechanism as described in U.S. Pat. No. 5,226,911. In the arrangement shown in FIG. 5, the distal section of guidewire 102 has an outer sleeve 110', comprising TEFLON or other appropriate insulating material, which is longer than sleeve 110 in FIG. 3.

Although implant 104 is shown as a vasoocclusive coil, it may take other forms. It can be a vasoocclusive braid, for example. Vasoocclusive device 104 also may be covered or connected with fibrous materials tied to the outside of the coil or braided onto the outer cover of the coil as desired. Such fibrous adjuvants may be found in U.S. Pat. No. 5,382,259, or in U.S. Pat. No. 5,226,911, the entirety of which are incorporated by reference.

After the vessel has been constricted, the coil is detached from the delivery wire. Preferably, AC generator 4 is electrically decoupled from guidewire 102 and DC power with AC superposition is supplied to the sacrificial link. The DC power input facilitates electrolysis of link 106 and, thus, detachment of the coil, while the AC power provides a signal to monitor and detect detachment. More specifically, the voltage or current amplitude of the AC signal is monitored so that the DC power input can be interrupted in response to detecting a sudden change in the AC signal amplitude. If the DC power source is of a constant current design, the voltage amplitude of the AC signal would be monitored. If the DC source has a constant voltage output, the current amplitude of the AC signal provides the desired change. A preferred embolic device detection circuit (EDDC) is described below.

Figure 6:
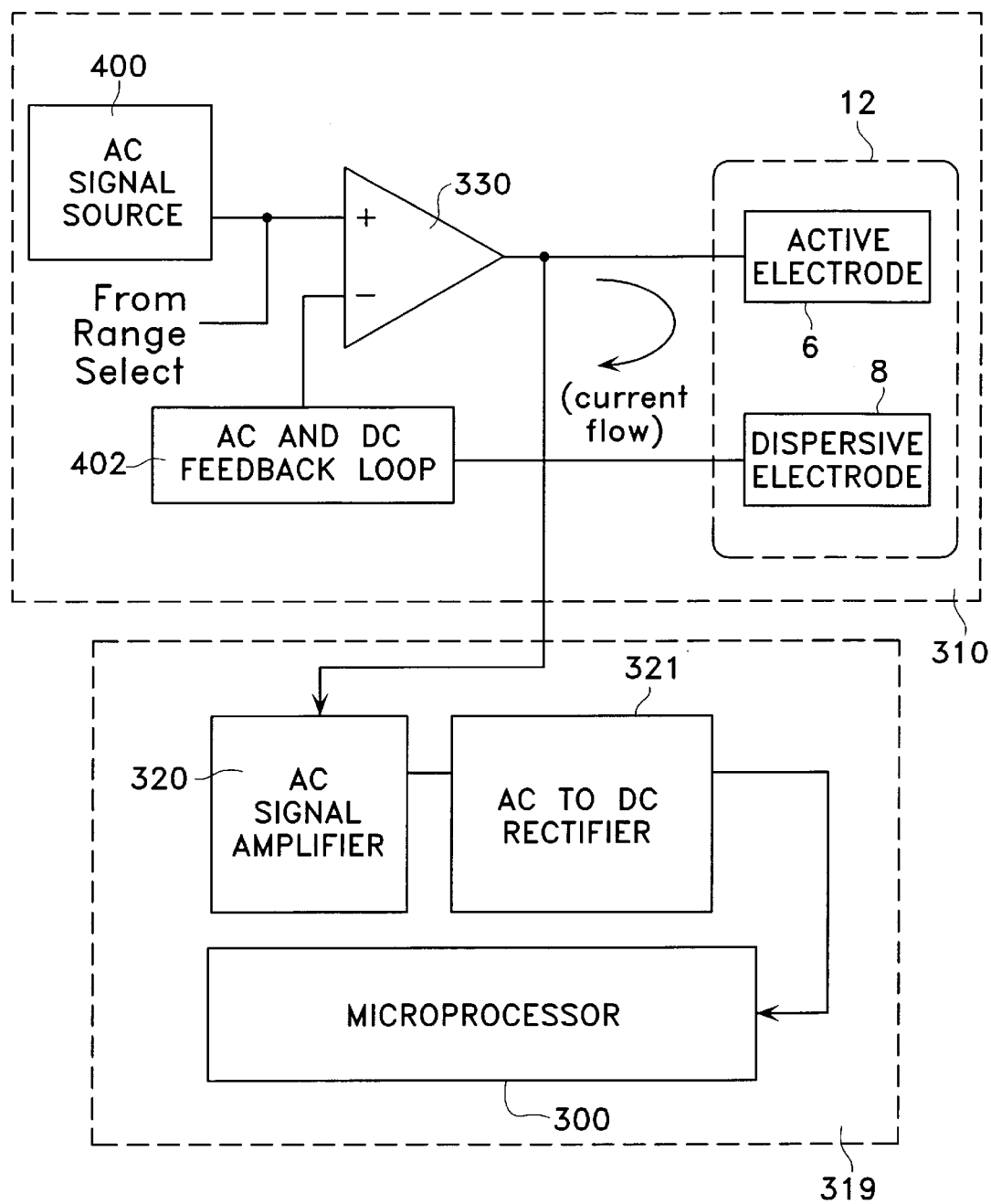
FIG. 6 is a block diagram of a power drive delivery and detection circuit for detecting electrolytic separation of an occlusion device.

Referring to FIG. 6, a constant current drive circuit and feedback loop 310 and an EDDC 319 for inducing and detecting the electrolytic separation of an occlusion device from a delivery member or guidewire are shown. The EDDC includes an AC impedance monitoring circuit and a circuit for detecting changes in the monitored impedance which can comprise microprocessor 300 as will be described in more detail below. The power supply and detection circuit (310, 319) provide a means to supply DC power with AC superposition and directly monitor the AC impedance by observing the reaction of amplifier 330 in response to the change in AC impedance.

Figure 7:
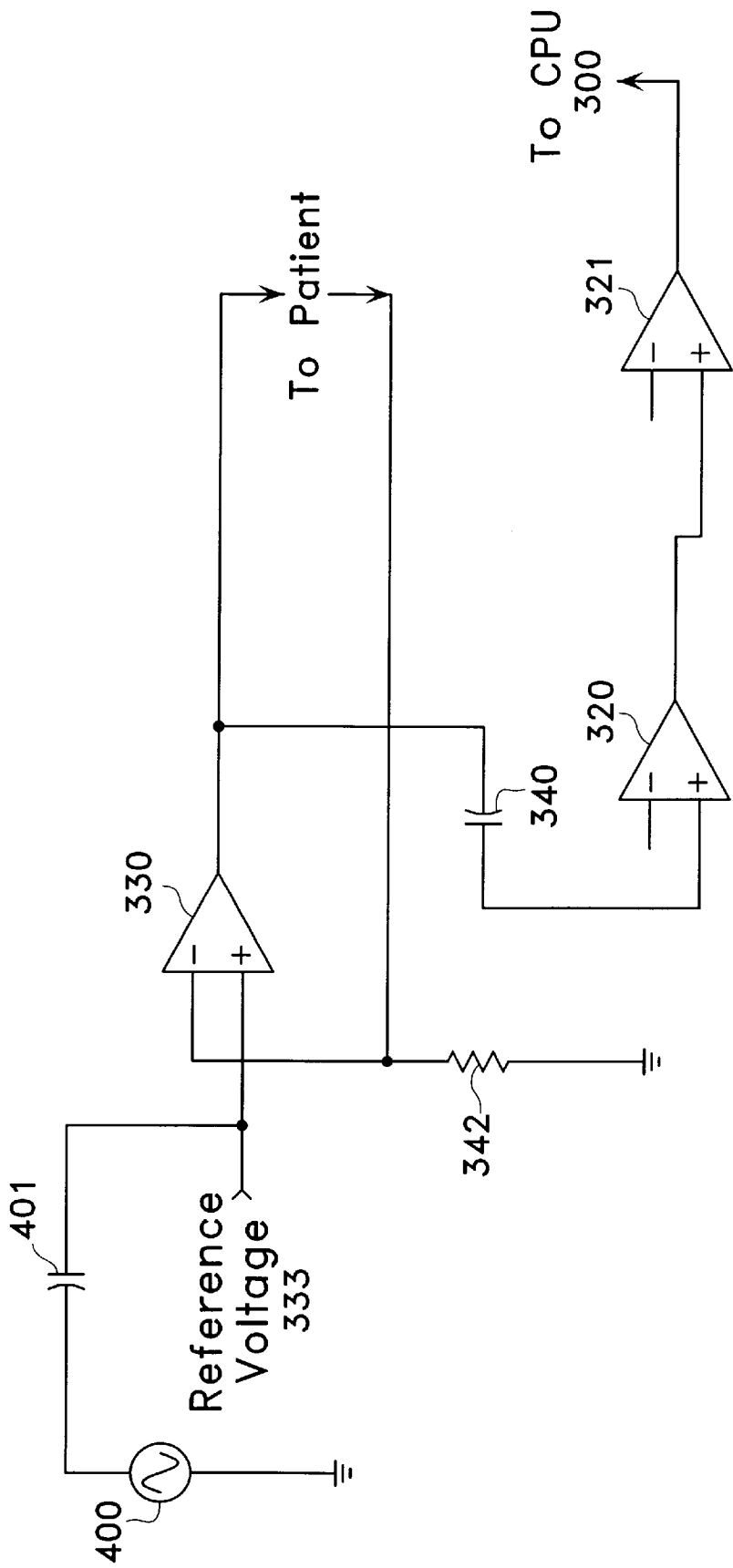
FIG. 7 is a schematic representation of the block diagram of FIG. 6.

Referring to FIG. 7, AC signal source 400 is coupled to the reference input of amplifier 330 so as to modulate the output current (i.e., provide AC superposition on the DC current). For purposes of example, a 31.25 kHz 100 mV peak-to-peak sine wave has been found to be a suitable input to the amplifier. Capacitor 401 is provided between AC signal source 400 and amplifier 330 to isolate DC bias from the AC signal input. Reference Voltage 333 and current sense resistor 342 and amplifier 330 comprise a constant current drive circuit. One suitable amplifier is a TI2274N amplifier manufactured by Texas Instruments.

In operation, an AC signal is provided to the non-inverting input of amplifier 330 where it is summed with the DC current reference. DC current with AC superposition is output from amplifier 330 and sent to the sacrificial link (e.g., link 106) shown in FIG. 4, which is coupled to the power supply. The DC and AC current paths branch. The DC current flows from the sacrificial link without passing through the coil, while the AC signal continues through the coil. These current paths rejoin at the patient return electrode and continue to AC and DC feedback loop 402. The AC signal is monitored at the output of the constant current amplifier where a measurement of AC impedance can be made through EDDC 319.

The amplitude of the AC signal is monitored through pick-off capacitor 340 FIG. 7, in this case, a 0.1 microfarad monolithic capacitor. The AC signal from capacitor 340 is then amplified in the AC signal amplifier 320, and is rectified and the peak detected in the AC to DC rectifier 321. The DC signal, the level of which is representative of the amplitude of the AC voltage of constant current amplifier 330 is then sent to the microprocessor (CPU) 300 for monitoring and analysis as described below.

The AC signal, which in the illustrated embodiment described above is voltage, is monitored by sampling the level of the amplified DC signal every 10 to 250 milliseconds, preferably every 50 to 200 milliseconds, and constantly averaging the signal every 5 to 50 samples, preferably every 10–20 samples or every 0.5–10 seconds, more preferably every 2–6 seconds. In this manner, the CPU can accurately determine the instant the occlusion device detaches as discussed below.

When the occlusion device detaches, constant current amplifier 330 instantly reacts to the change in AC impedance. The voltage amplitude of the AC waveform increases in an attempt to maintain the constant AC current set at the non-inverting input. During this period the amplified EDDC signal will show a sudden voltage increase of greater than 20%, preferably an increase of greater than 30% of the average level for the procedure. This sudden voltage increase reliably detects the dissolution of the junction between the embolic device and the guidewire.

When the sudden voltage increase is detected, the microprocessor immediately halts current flow, and no further electrolysis can occur. Using fluoroscopy, the physician can verify that detachment has occurred. If detachment is incomplete and further electrolysis is necessary, the procedure can be resumed by pressing the current-select switch on the front panel. If detachment is verified, the physician can turn off the power supply and withdraw the guidewire. If necessary, another coil can be placed at the site and the power supply started again. If no action is taken, the power supply will automatically turn itself off after 15 minutes.

Figure 8:
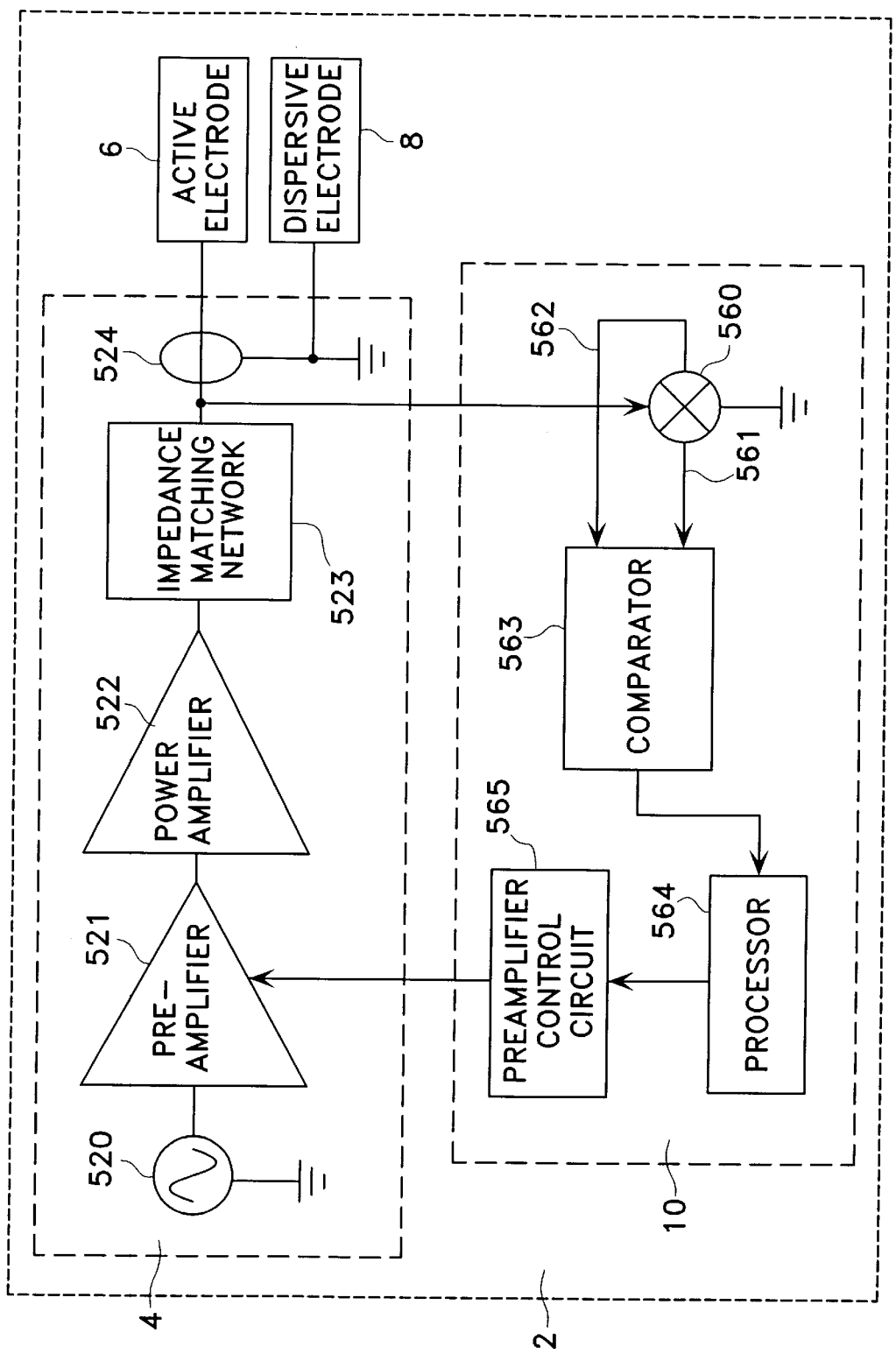
FIG. 8 diagrammatically shows a preferred embodiment of the apparatus of FIG. 1.

Referring to FIG. 8, a preferred RF power delivery and reflected power monitoring apparatus 2 is shown. Apparatus 2 comprises both an RF power source or generator 4 and reflected power monitoring circuit 10. RF generator 4 is the portion of the apparatus 2 designed to supply RF power to the target site.

RF generator 4 includes oscillator 520, preamplifier 521, power amplifier 522 and impedance matching network 523. Oscillator 520 is a sinusoidal (or filtered square wave) oscillator preferably operating at a frequency of 4 MHz (as discussed above). Oscillator 520 drives preamplifier 521 which amplifies the signal enough to drive the power output amplifier 522. The power output amplifier must be able to supply power to occlusive device 6 (which forms an active electrode) to provide an effective power density as discussed above. Conventional impedance matching network 523 defines the source impedance of RF generator 4 (i.e., it is selected to provide the desired source impedance).

The desired source impedance can be selected to match or mismatch the load impedance to the impedance of the output amplifier 522. The load impedance comprises the impedance of transmission cable 524 (which in the illustrated embodiment is a coaxial cable), delivery wire 102, active electrode 6, dispersive (or return) electrode 8 and patient tissue and/or blood.

Mismatched impedance has been found to provide desirable results and advantageously provides a known change in both amplitude and direction of the reflected power and desirable sensitivity as will be described in more detail below. For example, a 50 ohm source impedance for a 90 ohm load impedance has been found to provide suitable results. On the other hand, matched generator-to-load impedance provides maximum power transfer between the RF generator and occlusive device or electrode 6.

Although a particular RF power delivery arrangement has been described, it should be understood that other arrangements and/or circuitry can be used to supply the desired RF power with the desired source impedance as would be apparent to one of ordinary skill.

Returning to FIG. 8, reflected power monitoring circuit 10 comprises feedback circuitry that determines when endoluminal or vascular occlusion (partial or complete) has occurred. This circuit includes directional coupler 560, which may be a balun transformer, for example. Directional coupler 560 is coupled to the juncture between the impedance matching network 523 and transmission cable 524 and separates incident (coupled) power (power generated by RF generator 4) from reflected (isolated) power (or power reflected from the load), designated with reference 561 and 562, respectively. The output of this coupler may be voltage or current (collectively, "power"), signals or phase signals. Signals 561 and 562 are sent to a comparator 563 to monitor changes in reflected power. Power not reflected back to the generator is absorbed in the patient.

In one embodiment, comparator 563 is a Voltage Standing Wave Ratio (VSWR) comparator. With the VSWR approach the voltage amplitude of reflected power signal 562 can be compared to the voltage amplitude of incident power signal 561 to determine the change in reflected power (either the rms, average or peak-to-peak voltage amplitudes, for example, can be compared). A change in the difference between these signals directly corresponds to a change in reflected power. For example, a 20% change in the difference between the amplitudes of these signals corresponds to a 20% change in reflected power. Comparator 563 sends a signal indicative of the amount of reflected power to processor 564. This is a differential comparator approach where the output of generator 4 need not necessarily be held constant, thereby permitting power output adjustments, for example, during the occlusion procedure.

Alternatively, reflected power signal 562 can be compared to a predetermined value. In this case, the incident power from generator 4 is held constant. The predetermined value corresponds to a baseline value which, in turn, corresponds to the reflected power at an early stage of the occlusion procedure (e.g., about 0.5 seconds after initial power delivery to electrode 6). Thus, the voltage amplitude of reflected signal 562 at that time can be selected as the predetermined or baseline value. A change in the amplitude of signal 562 from the baseline value directly corresponds to a change in reflected power (e.g., a 20% change in amplitude corresponds to a 20% change in reflected power). Comparator 563 can be designed to send a signal indicative of the percent change in reflected power to processor 564. Alternatively, comparator 563 can be designed to send a go/no-go signal to processor 564. In the latter case, the comparator would be selected or programmed to send a no-go signal to processor 564 when the percent change in reflected power deviates from the baseline value by more than about 20% and a go signal at all other times.

In a further embodiment, comparator 563 may be a phase comparator where incident phase signal 561 is summed with reflected phase signal 562. Due to their phase characteristics (i.e., the forward (0°) and reverse (180°) waves of these signals), a change in the amplitude of the summed signal directly corresponds to a change in reflected power. For example, a 20% change in amplitude corresponds to a 20% change in reflected power. The comparator sends a signal indicative of the amount of reflected power to processor 563. In this case, comparator 563 again is a differential comparator.

Processor 564 receives a signal from comparator 563 as discussed above. When comparator 563 is a differential comparator, processor 564 compares the signal indicative of the amount of reflected power to a predetermined or baseline value. The predetermined or baseline value corresponds to the reflected power of an early stage of the occlusion procedure as described above. When a difference of more than about 20% between the reflected power and a baseline value is detected, processor 564 sends a shutdown signal to preamplifier control circuit 565. Processor 564 is coupled to preamplifier control circuit 565 which sends a control signal to shut down preamplifier 521, which shuts off the signal to output amplifier 522, when the predetermined change in reflected power has been detected or has occurred.

In the case where comparator 563 sends a go or no-go signal to processor 564, processor 564 sends a shutdown signal to preamplifier control circuit 565 when it receives the no-go signal. It should be understood that other reflected power monitoring circuits can be used. For example, comparator 563 can be incorporated into processor 564.

In addition, preamplifier control circuit 565 may be used to send a small amount of power to the occlusion device or active electrode 6 prior to the application of full RF power to verify that the load impedance is within the expected range. In this manner, shorted or unconnected test clips 571 or 581 (shown in FIG. 9), which couple the generator to return electrode 8 and guidewire 102 and, thus, electrode 6), or a poorly connected dispersive electrode 8 can easily be spotted and corrected before becoming a safety hazard to the patient or hospital staff.

A change in reflected power indicates a change in load impedance as discussed above. Since essentially only the impedance at the interface between active electrode 6 and immediate blood and/or tissue changes (FIG. 9), any monitored change in reflected power essentially corresponds to a change in power reflected back from the occlusive device. A change in reflected power of about 20% indicates that the occlusive device has become permanently embedded in the lumen wall, as will be discussed in more detail below. Whether the lumen or vessel wall has constricted such that its entire inner circumference has come in contact with the occlusive device depends on vessel size.

Figure 9:
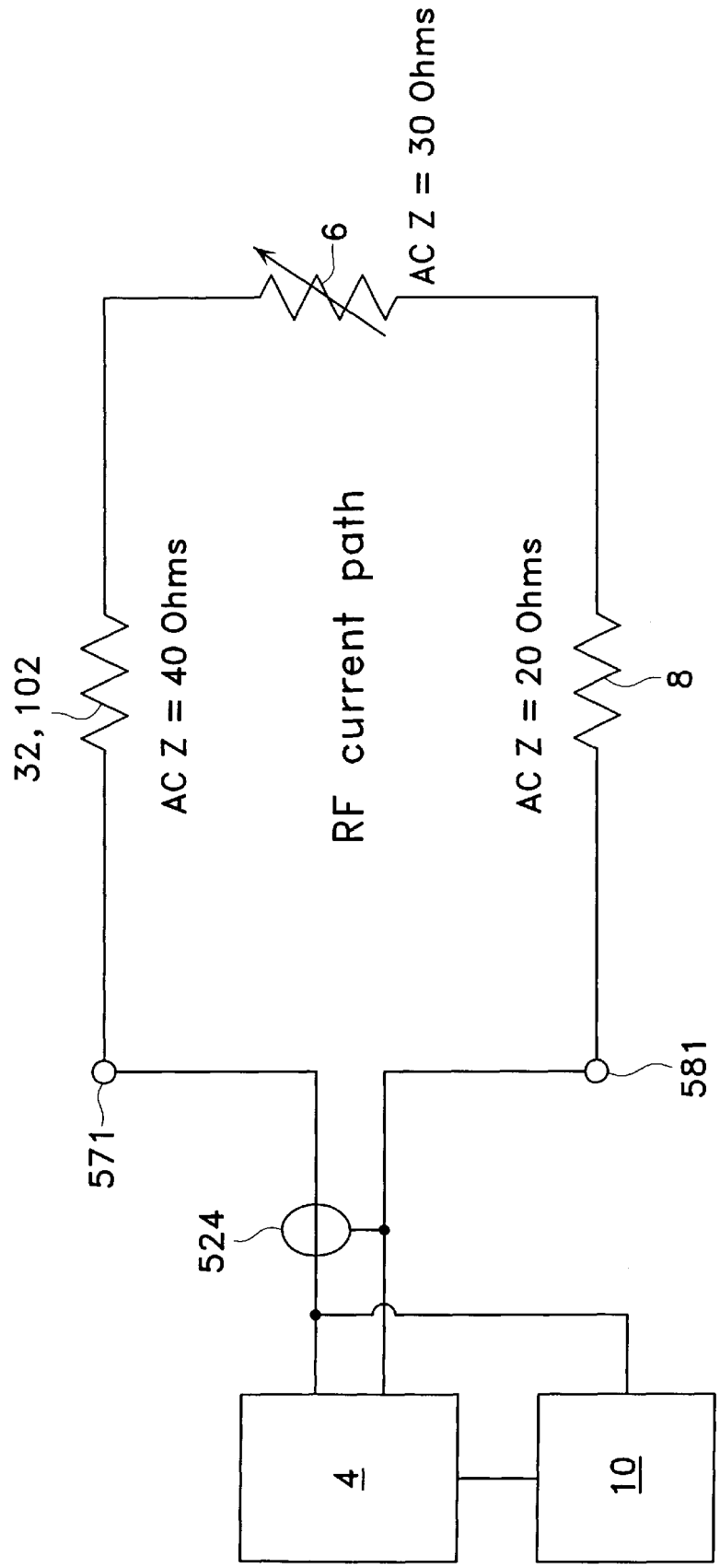
FIG. 9 schematically shows a load diagram for the apparatus of FIG. 1.

FIG. 9 schematically shows a load diagram for apparatus 2. Test clips 571 and 581 allow facile connection of the RF transmission cable 524 to the guidewire 102 (and, thus, to active electrode 6) and to dispersive or return electrode 8. Impedance (Z) values shown are typical during application of RF power prior to vascular occlusion and can represent typical baseline values. As should be obvious from the values shown, a 100% increase in the impedance at the occlusion site changes the load impedance by less than 100%. Therefore, there is need for a sensitive load impedance detector. The reflected power monitoring circuit described above provides such sensitivity. A more detailed description of reflected power follows.

Reflected power is the component of output power from an AC power generator that is not absorbed by the load in the circuit, but instead is reflected back from the load to the source generator. Where the source generator sends an oscillating signal of output power having a given magnitude, frequency and phase, the load acts as a source for the reflected power sending the signal back to the source generator at either the same or different magnitude and/or phase as the output signal. The combination of output power signal and reflected power signal in the circuit creates a standing wave pattern of energy between the source and the load. Reflected power monitoring circuits are generally designed to dissect the standing wave into the reflected power signal component and the output power signal component.

Reflected power is a function of load and source impedances, impedance being a function of resistance together with reactance (a frequency dependent parameter). The relationship of reflected power to the impedance of an AC circuit load depends upon the degree of matching of the source impedance of the generator to the impedance of the load. If there is impedance matching (if the source impedance matches or equals the load impedance) all of the power emitted from the source generator is absorbed by the load and there is no reflected power (similar to DC circuits). In contrast, if the source impedance is mismatched to the load impedance (if they are not equal) then the output power is only partially absorbed by the load and the remainder is reflected back to the source in a reflected power signal which can be monitored. Also, as impedance involves the frequency dependent reactance of the load, a given RF generator power source and a given load can have impedance matching only at a specific frequency. The relationship between impedance matching and reflected power in RF circuitry is well described by Chris Bowick in "RF Circuit Design", Howard W. Sams & Co., ISBN 0-672-21868-2 (1982–1993), at pages 66–67.

Figure 10:
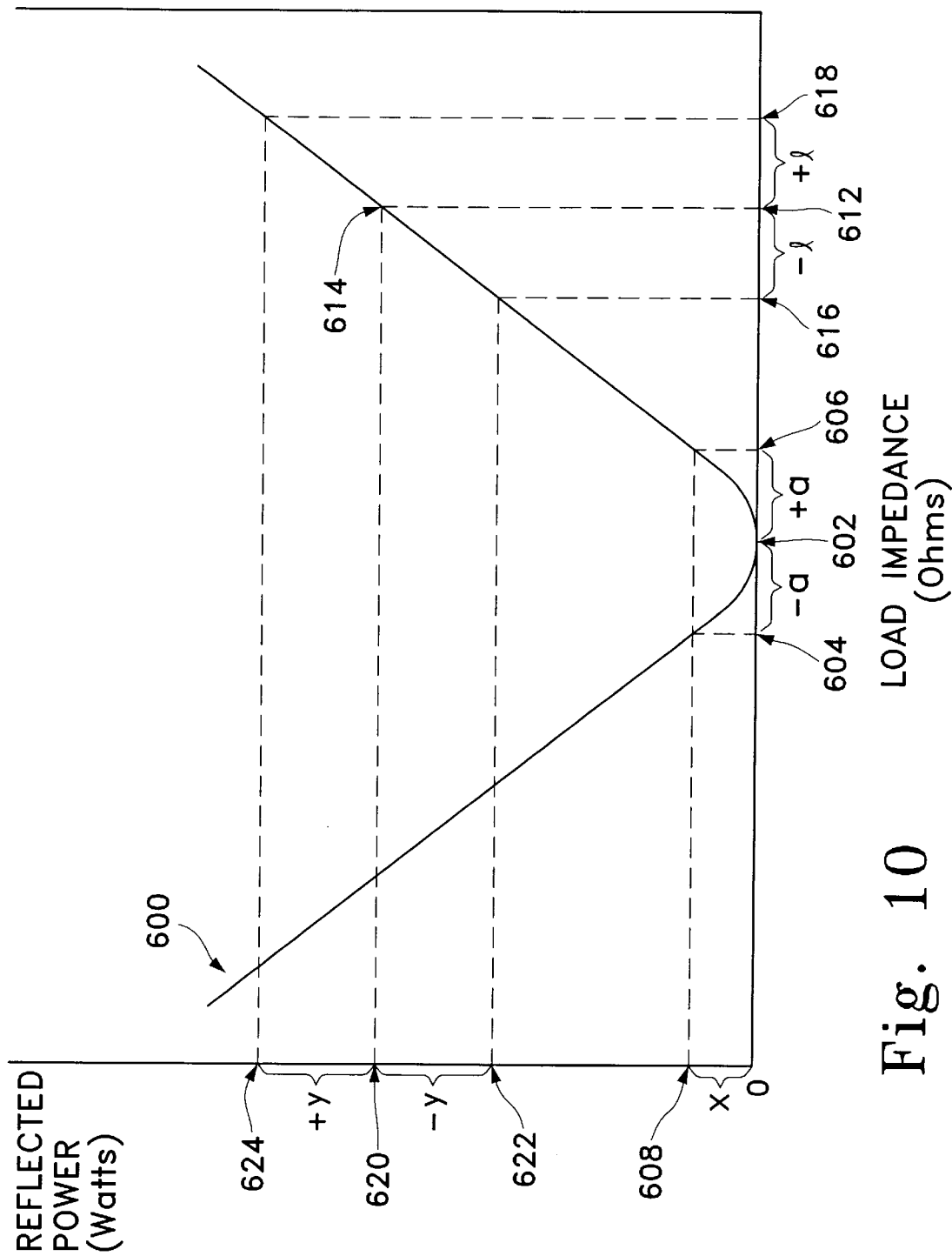
FIG. 10 graphically illustrates the relationship between reflected power vs. load impedance.

Referring to FIG. 10, a graph of reflected power vs. load impedance is shown. In this example, curve 600 can be reflected power vs. load impedance for a generator 4 having a source impedance of 50 ohms and where points 602 and 612 represent 50 and 90 ohms, respectively. (In the tests discussed below, these operating parameters were used.) Generally, the mismatched region is where the percent change in reflected power is directly proportional to the change in load impedance.

The nadir or minima 602 of curve 600 in FIG. 10 designates the operating relationship of reflected power vs. impedance when there is impedance matching. The load impedance shown at 602 matches the source impedance. At this point, all the output power from the RF generator is absorbed by the load and the reflected power signal for monitoring purposes is zero. That is, when impedance is matched, there is 100% absorption of the power output signal by the load. This mode of operation in the current invention allows the use of the lowest power generator capable of producing the desired occlusion response in tissue surrounding the electrode. With the approximate load impedance values shown for example in FIG. 9, the source impedance would have to be approximately 90 ohms in order to achieve impedance matching and operate at nadir 602.

Impedance of tissue closely surrounding occlusion device or active electrode 6 is a part of the load impedance as shown in FIG. 9. This impedance changes or shifts during RF electro-occlusion. If the RF generator were chosen to have a source impedance to match the baseline load impedance (the impedance measured at some time interval shortly after applying power to the electrodes and preferably before the load impedance begins significantly changing, preferably about 0.5 seconds after applying power to the electrode), then the load impedance shift away from the baseline can be represented either by moving from 602 to 604 (decrease), or from 602 to 606 (increase). Once this shift occurs, there is no longer impedance matching, but instead the circuit becomes mismatched (since the source impedance stays constant). A reflected power signal would be thus observed based on the relationship established by curve 600.

Referring to FIG. 10, a decrease (−a) in load impedance from point 602 to 604 on the graph corresponds to an increase (x) in reflected power from zero to some positive value shown at 608. Similarly, an increase (+a) in load impedance from matching point 602 to mismatched point 606 corresponds to the same increase (x) in reflected power from zero to the same positive value, shown also at 608.

Point 614 on curve 600 represents an alternative reflected power/load impedance relationship when the source is chosen to have baseline impedance mismatching, rather than baseline impedance matching as was just illustrated. Here the baseline load impedance is shown at 612, and corresponds with a baseline reflected power signal shown at 620. A decrease (−l) in load impedance from baseline point 612 to 616 on the graph corresponds to a decrease (−y) in reflected power from 620 to 622. An increase (+l) in load impedance from baseline point 612 to 618 corresponds to an increase (+y) in reflected power from 620 to 624. Thus, when the load impedance shifts away from its baseline value in this second illustration, the reflected power signal has a directly relational shift, both in magnitude and in direction.

It is believed that the direction of impedance shift may correspond to different types of occlusive responses in tissue. For example, a thrombogenic response onto the electrode surface and/or carbonized tissue contact with the electrode surface will result in an overall increase in impedance. This may be the primary occlusion response to RF electro-occlusion. Alternatively, non-carbonized, collagen-based tissue constriction onto the active electrode may cause a decrease in impedance. Such varying responses may prove to indicate varying medical treatments following an RF electro-occlusion procedure. The baseline impedance mismatch scheme of the second illustration enables the recognition of a directional impedance shift via monitored changes in the reflected power signal. Also, the baseline impedance mismatch point 612 is on a steeper slope of curve 600 when compared to the changing slopes at impedances closely surrounding the baseline impedance matching point at nadir 602. This steeper slope may allow for a more sensitive reflective power monitoring system as relates to small changes in load impedance.

Figure 11:
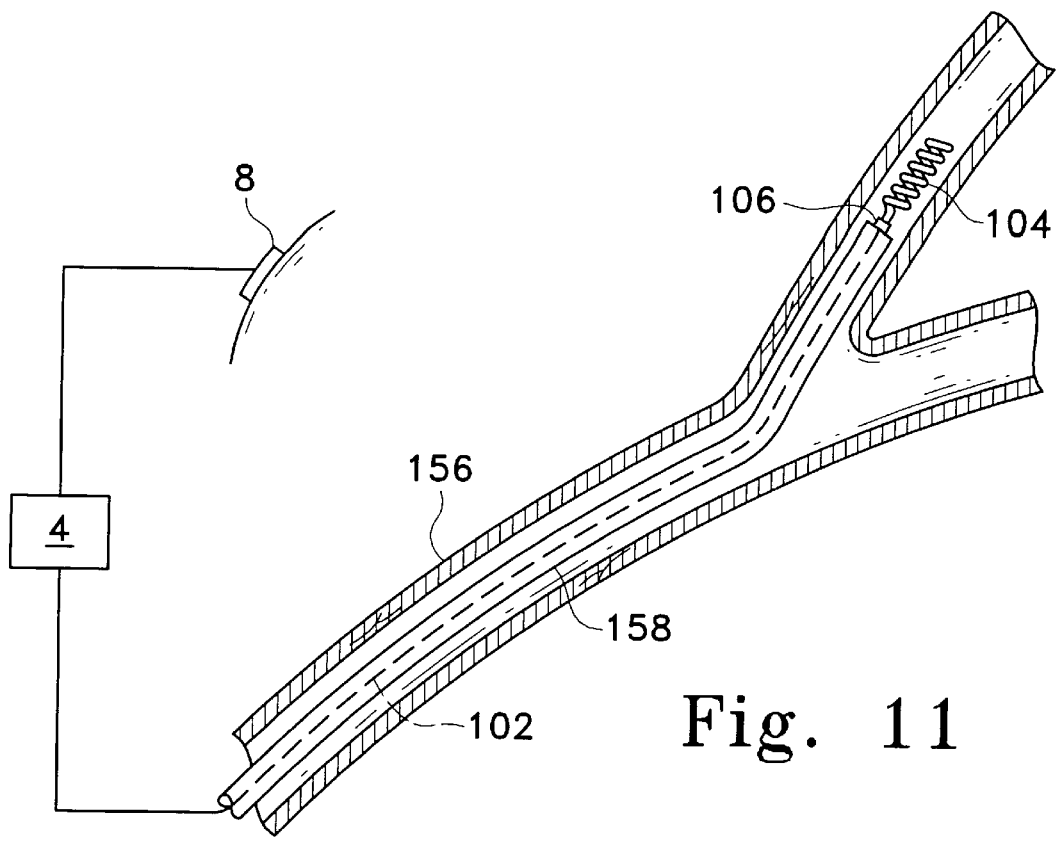
FIGS. 11 and 12 schematically depict the method for occluding a vessel according to the present invention.
Figure 12:
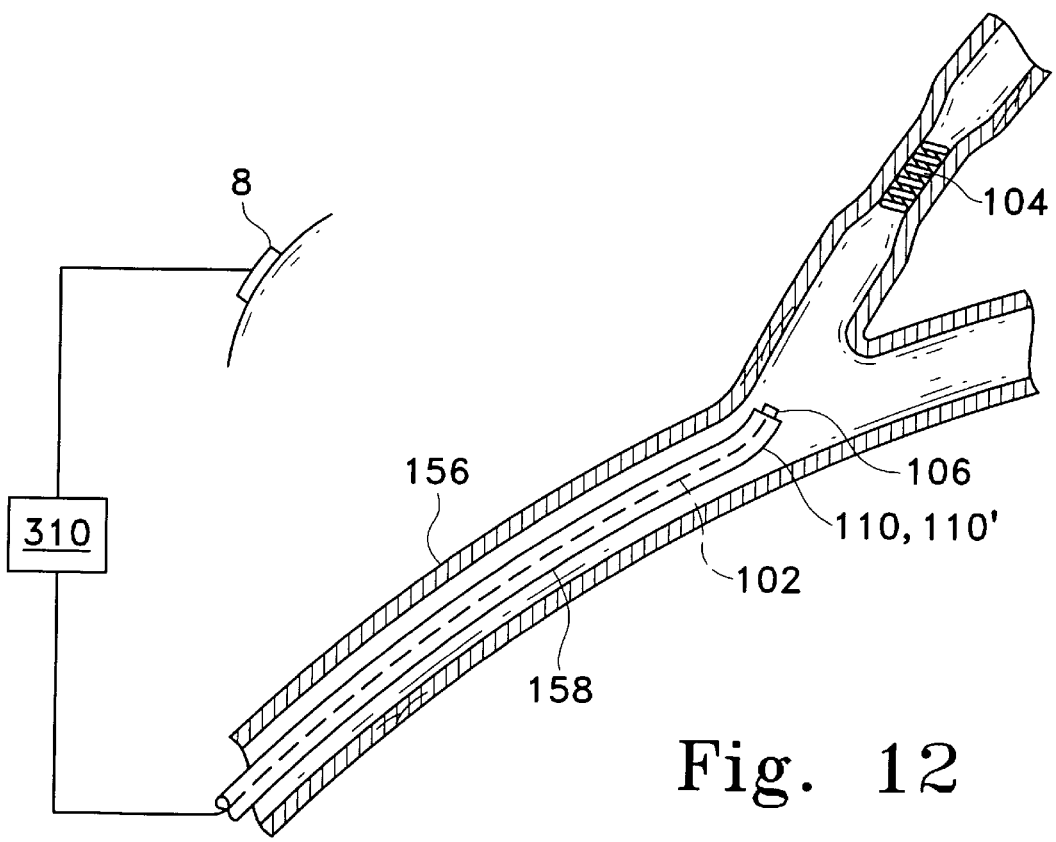

Referring to FIGS. 11 and 12, an example of the methodology of the present invention will be described. A site to be occluded is selected through the vasculature so that the distal end of the catheter is at or near the selected site using conventional techniques. One suitable catheter is the TRACKER endovascular catheter manufactured by Target Therapeutics, Inc. of Fremont, Calif. The implant, such as coil 24 or 104, is advanced through the catheter to the desired site via a delivery wire, such as delivery wire 32 or 102. The coil is positioned such that a portion of it contacts the vessel wall as shown in FIG. 11. This can be confirmed with conventional tactile or fluoroscopic techniques. The curvature of the coil, which will be discussed in more detail below, also will provide an additional indicator of the coil position. It is noted that in small vessels, e.g., vessels having a diameter of about 0.4 to 0.8 mm, coil to vessel contact will naturally occur.

Return or dispersive electrode 8 (which preferably is in the form of a large conductive pad) is provided to the patient with the lead coupled to one terminal of the RF generator 4. The other terminal of the RF generator is coupled to the proximal end portion of the delivery wire (32,102). An RF signal is then delivered to the coil to effectively heat the vessel for constriction around the coil (FIG. 11).

As discussed above, the RF power dielectrically heats the environment around the occlusive device or detachable coil to a temperature of about 50 to 120° C. and preferably about 70 to 100° C. At this temperature, the vessel constricts and the blood coagulates. It is believed that this vessel constriction is due to shrinkage of collagen components in the tissues surrounding the lumen. It is believed that about 0.1 to 10 watts at a frequency of about 100 KHz to 10 MHz at the coil provides the desired results with a 6 mm coil as described above. The following power delivery data is provided for illustrative purposes, and is not intended to limit the invention.

The reflected power monitoring circuit 10 takes a baseline reading of the power reflected from the load as described above over the first 0.5 seconds of power delivery. Processor 564 is programmed or selected to shut off RF generator 4 when a predetermined reflected power change has occurred. It has been found that a reflected power change of about 20% or more indicates that the coil has become embedded in the vessel wall and at least a portion of the vessel wall has constricted therearound. For instance, this may occur when a change in reflected power of at least about 20% is detected by comparator 563 and/or processor 564. Occlusion can then be verified using conventional fluoroscopic techniques to detect the absence of blood flow.

The following data were gathered from a number of tests on porcine vasculature using the electrolytic coil assembly and 50 ohm RF generator as described above with a reflected power monitor without the generator shutdown circuit.

Electrolytically detachable platinum coils, each having a length of 6 mm with a paralene coated tip length of 1 mm, helix diameter of 0.25 mm and a wire diameter of 0.05 mm were selected. Each coil was positioned in an ascending cervical artery in a pig. In more than half the tests, the inner diameter of the artery at the occlusion site varied from about 0.3 to 0.7 mm in various tests. In these tests, 5 watts (89 mA at 56 Vpp) at 4 MHz from the generator provided 1.5 watts reflected power during tissue heating, and approximately 2.5 watts reflected power when complete occlusion occurred. In the other tests, the artery inner diameter ranged from about 0.8 mm to 2.5 mm. The RF power from generator 4 ranged from about 10 to 40 watts at a frequency ranging from about 1 to 6 MHz. Complete or partial occlusion was achieved. In some of the tests where the inner artery diameter exceeded about 1.5 mm and where the coil was known not to be in contact with the artery wall, no vessel constriction was achieved although the reflected power monitoring circuit indicated a substantial reflected power change. This is believed to have resulted from a carbonized blood film forming on the coil. These coils, however, were readily removed as they had not become embedded in the arterial wall.

After occlusion is verified, the coil is detached from the delivery wire as described above and shown in FIG. 12. It is noted, however, that when using an electrolytically detachable coil, the occlusion site is flushed with a saline solution to remove anionic fluoroscopic imaging medium and enhance the electrolytic properties of the fluid surrounding the sacrificial link. If partial occlusion occurred, such as in the case of treating large vessels as discussed above, additional coil(s) (mechanically or electrolytically detachable) can be implanted at the site.

It is contemplated that frequencies well above 4 MHz may be used if power losses in the transmission and guidewire at those higher frequencies can be controlled. In these cases, the guidewire may be a flexible micro-coaxial cable, microwave transmission stripline or constructed otherwise as may be appropriate to effectively transmit the selected power and frequency to the occlusive device.

Returning to FIGS. 4 and 5, coil 104 preferably has a curved distal end portion to facilitate steering at junctures in the vasculature, for example. A radius of curvature of about 5 mm to 30 mm has been found to provide desirable results. However, vasoocclusive device 104 preferably is extremely soft and its overall shape is easily deformed. When inserted within a catheter, vasoocclusive device 104 is easily straightened to lie axially within the catheter as shown in FIG. 4. The distal end of vasoocclusive device 104 preferably also has an end plug or tip 154 to prevent punctures of endolumenal structures. This tip preferably is insulated to avoid high power density contact with the vessel wall.

It is also important that coil 104 provides an effective power density at the tissue to facilitate effective vessel heating. Power densities preferably range from about 1 W/mm$^2$ to 30 W/mm$^2$ as discussed above and should be such as to eliminate or minimize the risk of vessel perforation. For example, if the surface area of the coil is too large, the power density may be so low as to provide insufficient heating for vessel constriction or stenosis. On the other hand, if the coil surface area is too small, the increased power transfer density may result in vessel perforation. An example of one suitable coil construction is provided below for illustrative purposes only and is not intended to limit the invention.

The overall axial length of the occlusive device may be in the range of 0.10 to 1 cm. The length is typically 0.25 to 0.75 cm, more preferably about 0.5 cm. The coil typically has between 10–75 turns per centimeter, preferably 10–40 turns per centimeter. Generally speaking, when the device is formed of a metallic coil and that coil is a platinum alloy or a superelastic alloy such as nitinol, the diameter of the wire will be in the range of 0.0005 and 0.006 inches. Wire of such diameter is wound into a primary form diameter of between 0.005 and 0.025 inches. For most neurovascular indications, the preferable device diameter is 0.010 to 0.018 inches. It should be noted, however, that each of the dimensions is provided only as guidelines and is not critical to the invention.

The insulation on tip 154 typically is a polymer such as polyethylene, polypropylene, polyurethane, polyethylene terephthalate, polyvinylchloride, or the like and may be applied by a number of procedures. They may be applied by shrink-wrapping the insulators onto the device in the form of tubing. The device may be dipped in molten polymer. The insulator may be sprayed on in the form of a suspension or latex. Each of these procedures and polymers has benefits and detriments, e.g., added stiffness or complicated adjuvant process steps. One very desirable thermoplastic insulator is generically known as parylene. There are a variety of polymers (e.g., polyxylylene) based on para-xylylene. These polymers are typically placed onto a substrate by vapor phase polymerization of the monomer. Parylene N coatings are produced by vaporization of a di(P-xylylene) dimer, pyrolyzation, and condensation of the vapor to produce a polymer that is maintained at a comparatively lower temperature. In addition to parylene-N, parylene-C is derived from di(monochloro-P-xylylene) and parylene-D is derived from di(dichloro-P-xylylene). There are a variety of known ways to apply parylene to substrates. Their use in surgical devices has been shown, for instance, in U.S. Pat. No. 5,380,320 (to J. R. Morris), in U.S. Pat. No. 5,174,295 (to Christian et al.), in U.S. Pat. No. 5,067,491 (to Taylor et al.) and the like. A coating of less than about 0.001" is highly desirable, preferably less than about 0.00075", e.g., about 0.0002". A parylene coating has the benefits of being very thin and very flexible. Because it may be applied in a vapor-phase process, the masking of the conductive region is easily accomplished during coating of the insulated regions. In general, the insulator preferably has a bulk resistance of 500 kilohms/cm or greater.

Throughout this application, various publications, patents are referred to by an identifying citation. The disclosures of these various references are hereby incorporated by reference into this application.

The above is a detailed description of particular embodiments of the invention. It is recognized that departures from the disclosed embodiment may be made within the scope of the invention and that many alterations and modifications may be made by those having ordinary skill in the art without departing from the spirit and scope of the invention set out in the claims. The full scope of the invention is set out in the claims that follow and their equivalents.

What is claimed is:

1. An apparatus for providing endoluminal occlusion in a mammalian body, comprising:
   an alternating current (AC) power generator having a frequency in the radio frequency range and having a pre-determined output signal for producing an occlusion when said generator is coupled to a first electrode and a second electrode to form in-part an electro-occlusion drive circuit;
   a first electrode electrically coupled to said generator;
   a second electrode electrically coupled to said generator and forming in-part with said generator and said first electrode an electro-occlusion drive circuit; and
   a reflected power monitoring circuit coupled to said electro-occlusion drive circuit for indicating endoluminal occlusion by monitoring a reflected power signal toward the generator from the first electrode when said first electrode energized with the output signal.

2. The apparatus of claim 1 wherein said reflected power monitoring circuit includes a control circuit that is coupled to said electro-occlusion drive circuit for altering the delivery of said output signal when a predetermined change in the reflected power signal occurs.

3. The apparatus of claim 1 wherein said reflected power monitoring circuit includes a control circuit that is coupled to said electro-occlusion drive circuit for interrupting delivery of said output signal when a predetermined change in the reflected power signal occurs.

4. The apparatus of claim 1 wherein said reflected power monitoring circuit includes a control circuit that is coupled to said electro-occlusion drive circuit for interrupting delivery of said output signal when at least about a 20% change in said reflected power signal occurs.

5. The apparatus of claim 1 wherein said reflected power monitoring circuit includes a circuit for comparing said output signal and said reflected power signal.

6. The apparatus of claim 1 further including an elongated delivery member having a distal end portion, and wherein said first electrode is detachably coupled to said distal end portion for implantation as an endoluminal occlusion device.

7. The apparatus of claim 6 wherein said first electrode is mechanically detachably coupled to said delivery member.

8. The apparatus of claim 6 wherein said first electrode is electrolytically detachably coupled to said delivery member.

9. The apparatus of claim 1 wherein said first electrode is adapted for use in a fallopian tube.

10. An apparatus for providing endoluminal occlusion in a mammalian body, comprising:

an alternating current (AC) power generator having a frequency in the radio frequency range and having a pre-determined output signal for producing an occlusion when said generator is coupled to a first electrode and a second electrode to form in-part an electro-occlusion drive circuit;

a first electrode electrically coupled to said generator;

a second electrode electrically coupled to said generator and forming in-part with said generator and said first electrode an electro-occlusion drive circuit; and a directional coupler coupled to said electro-occlusion drive circuit for indicating endoluminal occlusion by detecting a reflected power signal from the first electrode when said first electrode is energized with the output signal.

11. A method for occluding a lumen in a mammal, comprising the steps of:

(a) delivering an occlusion device to a desired site within the mammal;

(b) applying an alternating current signal to the occlusion device to form an occlusion;

(c) monitoring a reflected power signal from the occlusion device during step (b) in order to indicate endoluminal occlusion.

12. The method of claim 11 wherein step (c) further includes the step of identifying a baseline reflected power signal during an initial period of step (b), said method further comprising the step of:

(d) interrupting the application of alternating current to the occlusion device in response to a predetermined change in the monitored reflected power from the baseline signal.

13. The method of claim 12 wherein step (d) further includes the step of interrupting the delivery of AC to the occlusion device in response to a change in reflected power of at least about 20%.

14. The method of claim 12 wherein step (b) further includes delivering the AC signal to the occlusion device at a radio-frequency.

15. The method of claim 11 wherein step (a) comprises delivering the occlusion device to the desired site via a delivery member that is detachably coupled to the occlusion device.

* * * * *